(12) United States Patent
Orinski

(10) Patent No.: US 10,213,596 B2
(45) Date of Patent: Feb. 26, 2019

(54) SKULL-MOUNTED OPTICAL IMPLANT

(71) Applicant: Boston Scientific Neuromodulation Corporation, Valencia, CA (US)

(72) Inventor: William G. Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 16 days.

(21) Appl. No.: 15/470,653

(22) Filed: Mar. 27, 2017

(65) Prior Publication Data

US 2017/0281927 A1    Oct. 5, 2017

Related U.S. Application Data

(60) Provisional application No. 62/314,816, filed on Mar. 29, 2016.

(51) Int. Cl.
| | |
|---|---|
| *A61N 1/00* | (2006.01) |
| *A61N 1/05* | (2006.01) |
| *A61B 5/00* | (2006.01) |
| *A61N 1/36* | (2006.01) |
| *A61N 1/372* | (2006.01) |

(52) U.S. Cl.
CPC ............ *A61N 1/0534* (2013.01); *A61B 5/686* (2013.01); *A61N 1/0536* (2013.01); *A61N 1/0539* (2013.01); *A61N 1/3605* (2013.01); *A61N 1/36082* (2013.01); *A61N 1/37211* (2013.01); *A61N 1/0526* (2013.01); *A61N 1/0529* (2013.01)

(58) Field of Classification Search
CPC .. A61N 1/0534; A61N 1/0536; A61N 1/0539; A61N 1/3605; A61N 1/36082; A61N 1/37211; A61N 1/0526; A61N 1/0529; A61B 5/686
See application file for complete search history.

(56) References Cited

U.S. PATENT DOCUMENTS

| | | |
|---|---|---|
| 6,304,784 B1 | 10/2001 | Allee et al. |
| 6,921,413 B2 | 7/2005 | Mahadevan-Jansen et al. |
| 7,395,118 B2 | 7/2008 | Erickson |
| 8,761,889 B2 | 6/2014 | Wingeier et al. |
| 8,936,630 B2 | 1/2015 | Denison et al. |
| 2005/0075680 A1* | 4/2005 | Lowry ............... A61N 1/0531 607/45 |

(Continued)

OTHER PUBLICATIONS

Chung, Hoon, et al., "The Nuts and Bolts of Low-Level Laser (Light) Therapy," Ann Biomed Eng., 40(2), Feb. 2012, pp. 516-533.

(Continued)

*Primary Examiner* — Lindsey G Wehrheim
(74) *Attorney, Agent, or Firm* — Lewis & Reese, PLLC

(57) ABSTRACT

A skull-mountable medical device is disclosed. The device includes a housing containing a light source for providing phototherapy to a patient. A light pipe is attached to the housing. The device is configured to be positioned on a patient's skull with the light pipe extending into the patient's brain, such that light from the light source can irradiate a target position within the patient's brain. Once so positioned, the housing may be affixed to the skull via bone screws. The device is powered and controlled by an implantable pulse generator (IPG) that may be implanted into a patient's tissue remotely from the device and connected to the device by wire leads.

20 Claims, 7 Drawing Sheets

Fig. 1B

(56) References Cited

U.S. PATENT DOCUMENTS

| | | | |
|---|---|---|---|
| 2009/0054955 A1* | 2/2009 | Kopell | A61N 5/0601 |
| | | | 607/88 |
| 2009/0088680 A1 | 4/2009 | Aravanis et al. | |
| 2011/0125077 A1* | 5/2011 | Denison | A61N 5/0601 |
| | | | 604/20 |
| 2012/0259393 A1 | 10/2012 | Benabid et al. | |
| 2013/0184794 A1 | 7/2013 | Feldman et al. | |
| 2013/0317575 A1 | 11/2013 | Deisseroth et al. | |

OTHER PUBLICATIONS

Darlot, Fannie, et al., "Near-Infrared Light is Neuroprotective in a Monkey Model of Parkinson's Disease," Annuals of Neurology, 79(1), Jan. 2016, pp. 59-75.

Desmet, Kristina, et al., "Near-infrared Light as a Possible Treatment Option for Parkinson's Disease and Laser Eye Injury," Proc SPIE—The International Society for Optical Engineering, vol. 7165, 2009, pp. 716503-716510.

* cited by examiner

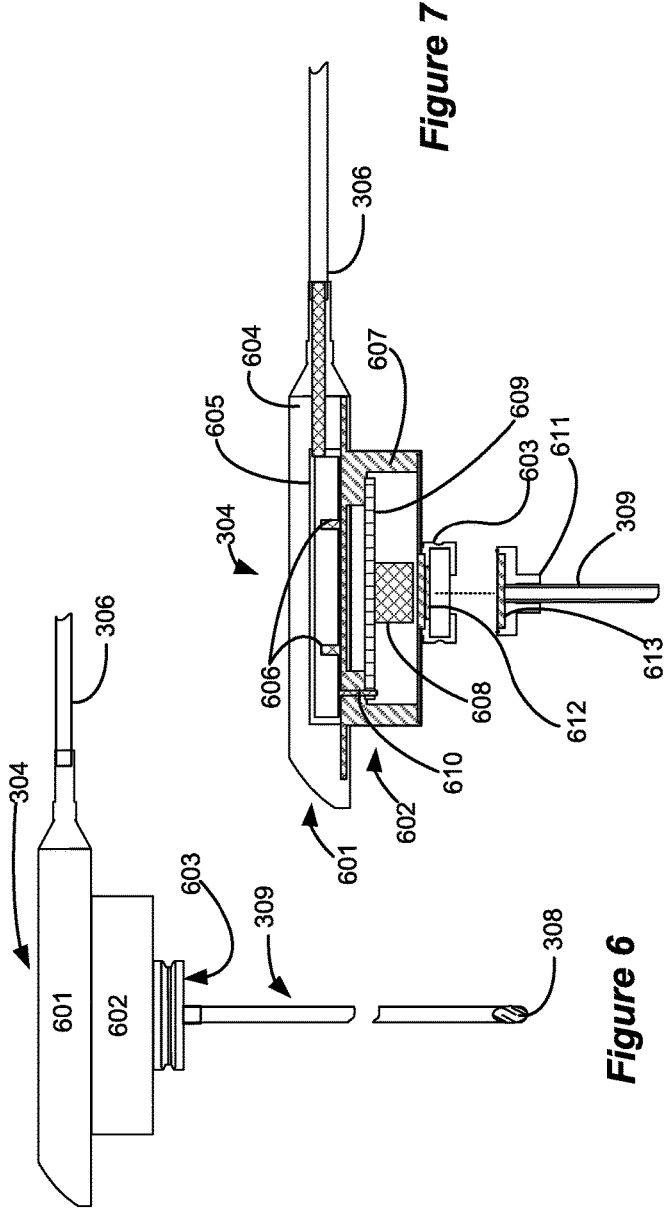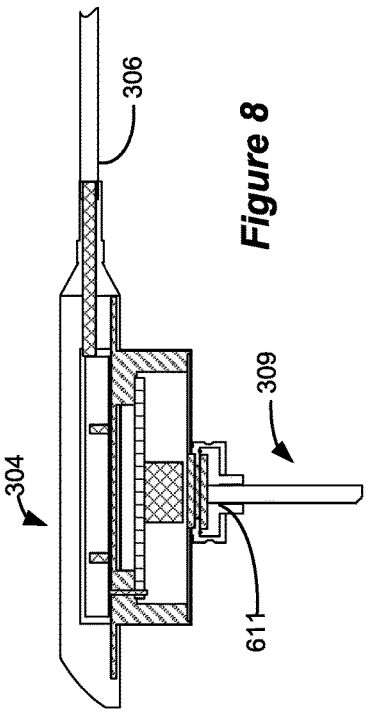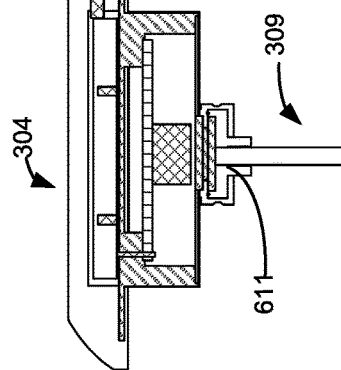

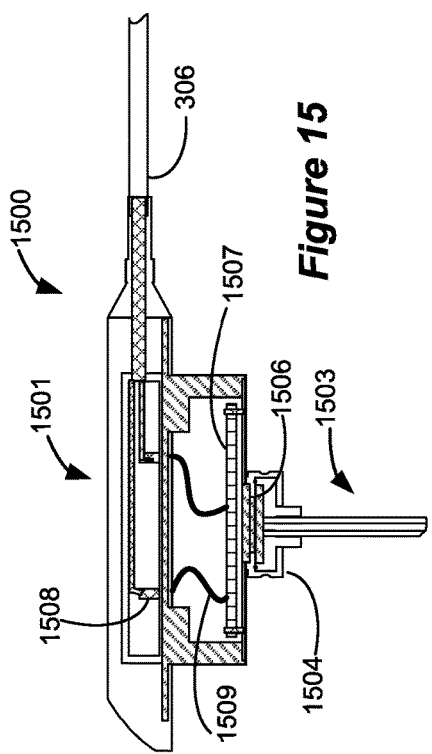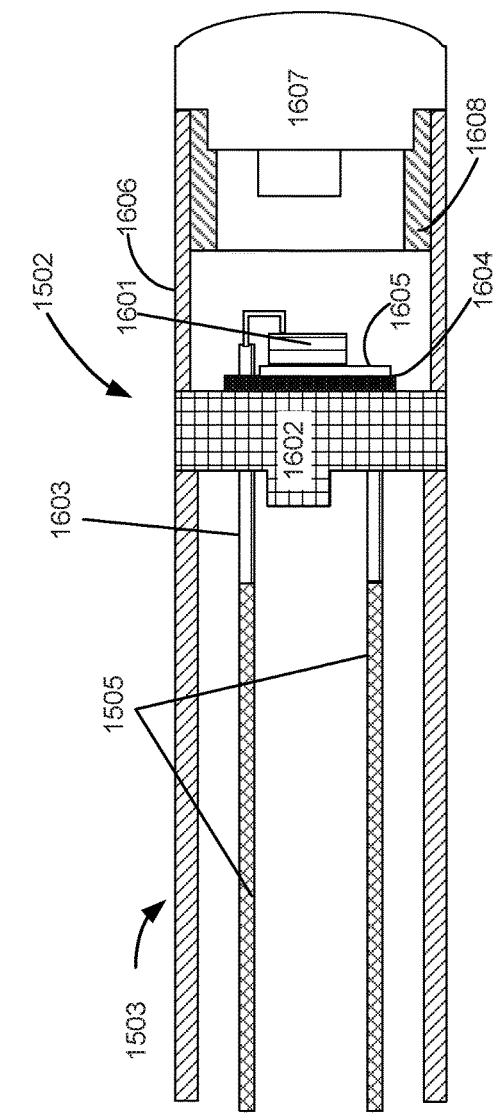

SKULL-MOUNTED OPTICAL IMPLANT

CROSS REFERENCE TO RELATED APPLICATIONS

This is a non-provisional application of U.S. Provisional Patent Application Ser. No. 62/314,816, filed Mar. 29, 2016, which is incorporated by reference in its entirety, and to which priority is claimed.

FIELD OF THE INVENTION

The present application relates to implantable devices, and more specifically, to a skull-mounted medical device for providing phototherapy to a patient's brain.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Deep Brain Stimulation (DBS) system. However, the present invention may find applicability with any Implantable Pulse Generator (IPG) or in any IPG system.

As shown in FIG. 1, a DBS system includes an Implantable Pulse Generator (IPG) 10, which includes a biocompatible device case 12 comprising titanium for example. The case 12 typically holds circuitry and a battery (not shown), which battery may be either rechargeable or primary in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 contacts the electrode terminals 20, and communicate with the circuitry inside the case 12 via feedthrough pins 26 passing through a hermetic feedthrough 28 to allow such circuitry to provide stimulation to or monitor the various electrodes 16.

In a DBS application, as is useful in the treatment of Parkinson's disease for example, the IPG 10 is typically implanted under the patient's clavicle (collarbone), and the leads 18 with electrodes 16 are implanted through holes drilled in the skull in the left and right and side of the patient's brain 32, as shown in FIG. 2. Specifically, the electrodes 16 may be implanted in the subthalamic nucleus (STN), the pedunculopontine nucleus (PPN), the Global Pallidus Interna (GPI), and/or the Ventral Intermediate Nucleus (VIM). In this regard, four leads 18 may be necessary for full coverage, as discussed further in U.S. Patent Application Publication 2013/0184794. Thereafter, a tunnel is formed under the patient's skin and fascia (e.g., over the skull, behind the patient's ear, down the neck) to connect the proximal ends of the leads 18 to the IPG 10. As the distance from the skull holes to the IPG 10 is rather long, extender leads 28 may be employed having receptacles 30 into which the electrode terminals 20 of the leads 18 can be inserted. The extender leads 28 have their own electrode terminals (not shown) to allow connection to the connector blocks 22 in the IPG 10.

While DBS therapy employed in the manner shown can provide symptomatic relief for a patient, it does not slow the underlying progression of the disease. Thus, treatment methodologies that not only provide symptomatic relief, but that also stop or slow the underlying neurological degeneration, are needed. Phototherapy, i.e., irradiating neurons with light, is one such treatment. For example, animal studies have shown that irradiating neurons with near-infrared (NIr) light can curtail degenerative processes within the neurons. See, e.g., Darlot, et al., Near-Infrared Light is Neuroprotective in a monkey model of Parkinson's disease, *Ann Neurol*, 2016, 79(1), 59-75; and Desmet, et al., Near-infrared Light as a Possible Treatment Option for Parkinson's Disease and Laser Eye Injury, 2009, *Proc SPIE-The International Society for Optical Engineering*, 716503-10. Thus, there is a need for medical devices for delivering phototherapy to neurons within a patient's brain.

BRIEF DESCRIPTION OF THE DRAWINGS

FIG. 6 shows an SMI.

FIG. 7 shows a cross-section cutaway view of an SMI.

FIG. 8 shows a cross-section cutaway view of an SMI.

FIG. 15 shows an SMI configured with a light source contained within an optical lead.

FIG. 16 shows a light source contained within an optical lead.

DESCRIPTION

Figure 4:
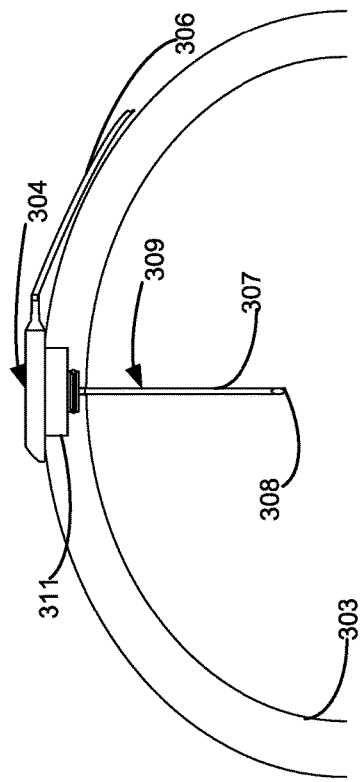
FIG. 4 shows an SMI attached to a patient's skull.
Figure 5:
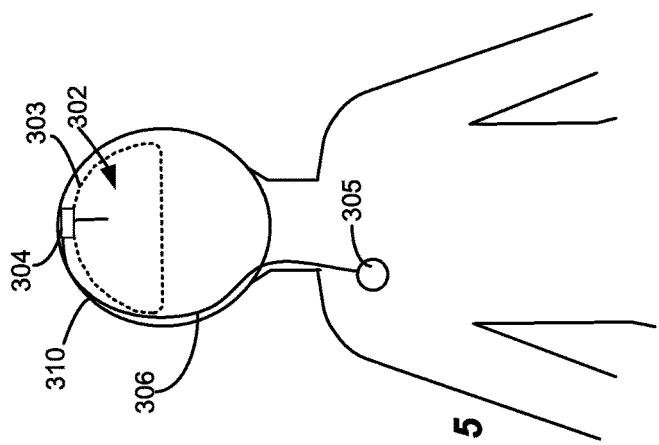
FIG. 5 shows an SMI connected to an IPG.
Figure 3:
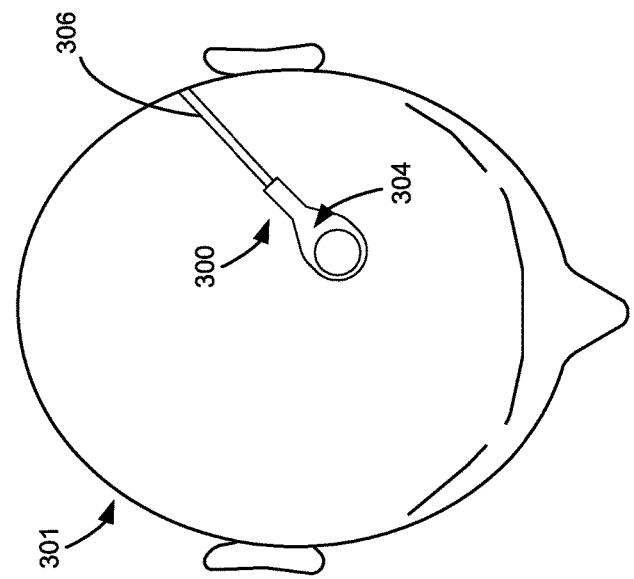
FIG. 3 shows a skull-mounted implant (SMI).

FIGS. 3, 4, and 5 show a skull-mounted implant (SMI) 300 for providing phototherapy to the brain 302 a patient 301. SMI 300 includes an implant housing 304 that is mounted to a patient's skull 303 and connected to an implantable pulse generator (IPG) 305 by a power lead 306 whereby the SMI 300 receives power and programming data from the IPG 305. The implant housing 304 and the power lead 306 are typically placed between the patient's skull 303 and scalp 310. The IPG 305 is typically implanted in the patient's pectoral region or some other fleshy region.

As shown in FIG. 3, viewing the top of a patient's head, the implant housing 304 is designed to lie generally flat against the patient's skull, and preferably above the patient's ear proximate to the temporal or parietal bones. Such placement is preferable because the skull in these locations is generally flat, therefore allowing the implant housing 304 to lay relatively flat. However, because the implant housing 304 is flexible at certain locations, perfect flatness of the skull is not required.

The implant housing 304 includes a light source and supporting electronics for the light source, both of which are discussed in more detail below. The implant housing 304 attaches to a light pipe 309, which provides a path for therapeutic light to a target area of the patient's brain. The light pipe includes a tube 307 terminated by a diffuser 308.

Before securing of the implant housing 304 to the skull 303, the implanting physician will have drilled one or more holes in the skull and will have inserted the distal end of the light pipe 306 into an appropriate location in the brain 302. The physician can secure the properly placed light pipe 309 using standard means, such as by cementing or plugging. Thereafter, and once the physician has verified the effectiveness of neurostimulation therapy, the implant housing 304 can be secured to the skull. For example, the implant housing 304 may include one or more screw holes (or partial holes), as known in the art, to allow the implant housing 304 to be firmly secured to the skull with bone screws once it is correctly positioned. In FIG. 4, the hole 311 in the skull 303 for accepting the implant housing 304 proceeds only partially through the thickness of the skull 303, but in other examples may proceed all the way through to the dura (not shown) surrounding the brain 302.

FIGS. 6, 7 and 8 illustrate the implant housing 304 and related assemblies in greater detail. As illustrated in FIG. 6, the implant housing 304 includes a top portion 601 that fits outside of and against a patient's skull 303, a lower portion 602 that is embeds in the patient's skull, and a light pipe fitting portion 603 that is configured to attach the light pipe 309 to the lower portion 602.

FIG. 7 shows a cutaway view of the implant housing 304. The top portion 601 and a portion of the power lead 306 attaching to the top portion 601 can be sealed in an overmolding material such as silicone. The overmolding serves to integrate the implant housing 304 and the power lead 306 and also to provide soft surfaces for portions of the implant housing 304 that might come into contact with a patient's tissue/fascia. The overmolding 604 encloses a non-hermetically sealed top cover 605. According to some embodiments the top cover 605 is made of titanium. The top cover 605 encloses feedthroughs 606, whereby the power lead 306 makes electrical contact with a printed circuit board (PCB) 609 contained within the lower portion 602. The lower portion 602 includes a hermetically sealed housing 607 that encloses a light source 608 connected to the PCB 609. The hermetically sealed housing 607 may be made of a material such as titanium. The PCB 609 may be electrically grounded to the housing 607 by housing ground pin 610.

According to certain embodiments, the light source 608 is a light emitting diode (LED) or a laser diode. A physician may choose a light source 608 to provide a particular wavelength of light that the physician believes will be therapeutic. For example, the light wavelength be in the in the near-UV spectrum (~300-400 nm), the visible spectrum (~390-750 nm), or the near-IR spectrum (~750-1400 nm). Particular examples of light sources emit in a narrow band centered at about 670 nm or at about 740 nm. An example of a suitable light source the Ushio HL6748MG, (Ushio OPTO Semiconductors, Inc.), which is a 670 nm/10 mW AlGaInP laser diode.

The light source 608 may be mounted to the PCB 609, which includes electronics for driving the light source 608. The PCB 609 may include additional electronics for operating and controlling the SMI. For example, the PCB 609 may be connected to a temperature sensor within the hermetically sealed housing 607. Such a temperature sensor may be configured to monitor the temperature of the housing and to interrupt power to the light source 608 if the temperature exceeds a certain value.

The light pipe fitting 603 is mounted to the bottom of the lower portion 602 and is configured to receive a light pipe ferule 611, as illustrated in FIG. 8. According to some embodiments, the light pipe 309 is interchangeable with light pipes of different lengths, allowing the physician to choose the depth within the patient's brain to which light is delivered. The light pipe fitting 603 includes a glass window 612 that mates with a glass window 613 contained within the light pipe ferule 611. The glass windows 612 and 613 provide a path for light from the light source 608 into the light pipe 309.

Figure 9:
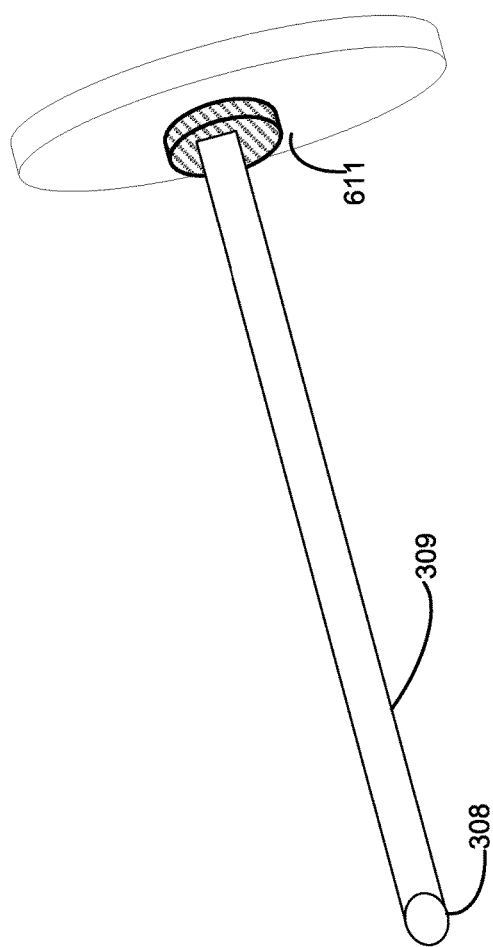
FIG. 9 shows a light pipe for an SMI.
Figure 10:
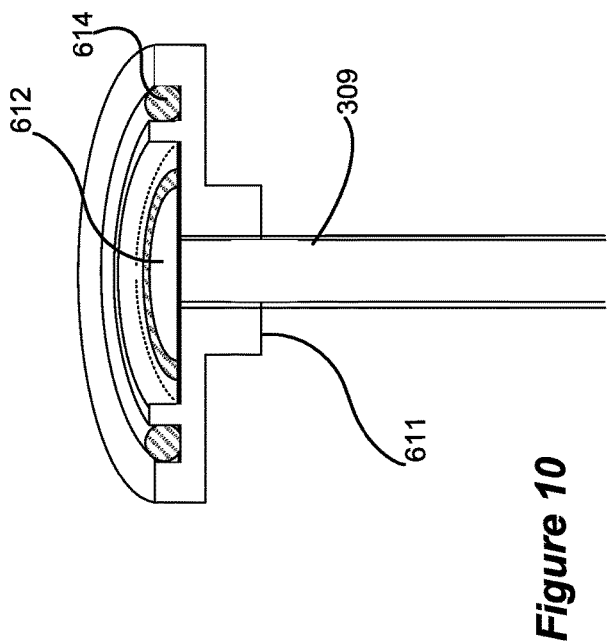
FIG. 10 shows a cross-section cutaway view of a light pipe for an SMI.

The light pipe 309 and light pipe ferule 611 are illustrated in more detail in FIGS. 9 and 10. According to according to certain embodiments the light pipe 309 is simply a tube that provides a path for from the light source 608. The tube may be of the material such as stainless steel. According to other embodiments described in more detail below the light pipe 309 may house a light guide such as an optical fiber. The light pipe ferule 611 may include an o-ring 614 to facilitate sealing the light pipe ferule 611 to the light pipe fitting 603. The light pipe 309 is terminated with a diffuser 308. The diffuser 308 serves to defuse light from the light source to cover a target area within the patient's body. A person of skill in the art will appreciate that light diffusers are available to provide many different irradiation patterns. For example a ball lens fiber to may provide a cone of irradiation extending from the tip of the light pipe 309. A side-fire diffuser provides irradiation extending laterally from the diffuser. A radial diffuser provides a spherical irradiation pattern. In alternative embodiments, a lens may be used in place of the diffuser, for example, to collimate or focus the light on a target area. A physician can choose a particular diffuser 308 to provide the particular irradiation pattern most suitable to his treatment plan.

Figure 11:
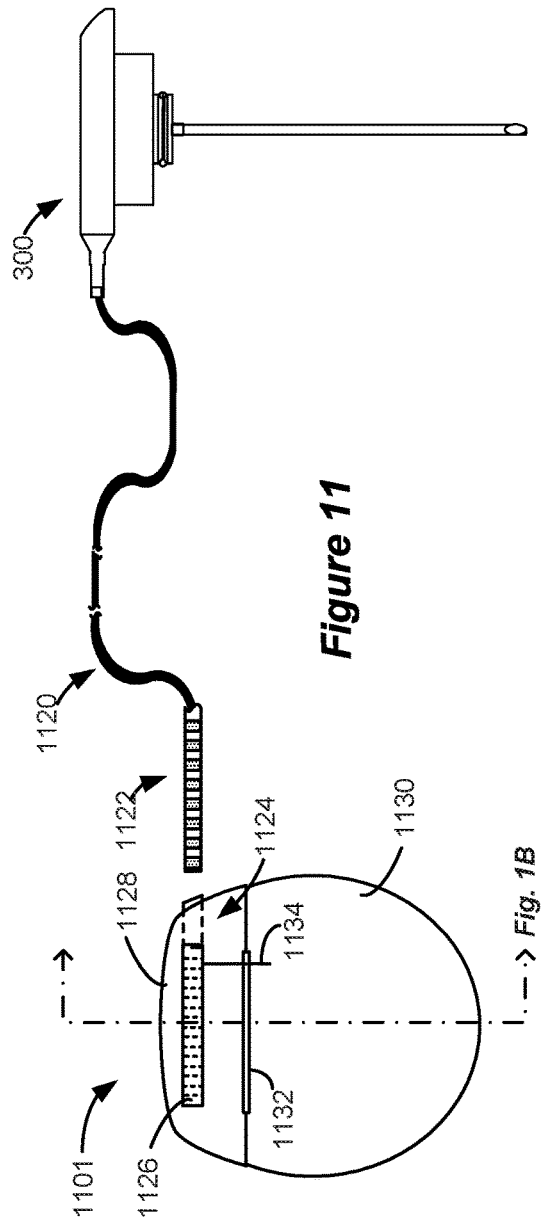
FIG. 11 shows an SMI attached to an IPG.

FIG. 11 illustrates an IPG 1101 for powering and controlling the SMI 300. Implantable Pulse Generator (IPG) 1101 shown in plan and cross-sectional views in FIGS. 11 and 12. The IPG 1101 includes a biocompatible device case 1130 that holds the circuitry and battery 1136 (FIG. 12) necessary for the IPG to function. The IPG 1101 is coupled to the SMI 300 via lead wires 1120. The lead wires 1120 are also coupled to proximal contacts 1122, which are insertable into lead connector 1124 fixed in and encompassed by a header 1128 on the IPG 1101, which header can comprise an epoxy for example. Once inserted, the proximal contacts 1122 connect to header contacts 1126 in the lead connector 1124, which is in turn coupled by electrode feedthrough pin 1134 through an electrode feedthrough 1132 to circuitry within the case 1130 (connection not shown). Case 1130 can be formed of case portions 1130a and 1130b (FIG. 12) which are laser welded together and to the electrode feedthrough 1132.

In the illustrated IPG 1101, there are eight proximal contacts 1122, with the header 1128 containing a single lead connector 1124 to receive the lead's proximal end. However, the number of leads and contacts in an IPG is application specific and therefore can vary. For example, some therapeutic applications may involve using traditional stimulating electrodes in conjunction with phototherapy. In such an application, the IPG 1101 may include additional lead connectors for receiving the electrodes. In the illustrated IPG 1101, the eight proximal contacts and corresponding leads may transmit power (positive and ground wires), data, and commands between the IPG 1101 and the SMI 300. Depending on the amount and type of data and commands, the number of leads and contacts may differ.

Figure 12:
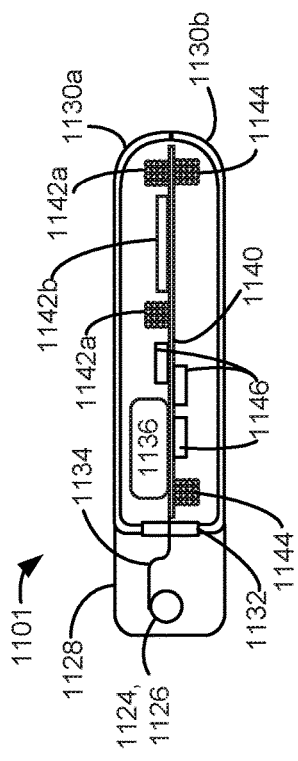
FIG. 12 shows an IPG for controlling and SMI.

As shown in the cross section of FIG. 12, the IPG 1110 includes a printed circuit board (PCB) 1140. Electrically coupled to the PCB 1140 are the battery 1136, which in this example is rechargeable; other circuitry 1146 coupled to top and/or bottom surfaces of the PCB, including a microcontroller and other circuitry necessary for IPG operation; a telemetry antenna—1142*a* and/or 1142*b*—for wirelessly communicating with an external device; a charging coil 1144 for wirelessly receiving a magnetic charging field from an external charger for recharging the battery 1136; and the electrode feedthrough pins 1134 (connection to circuitry not shown). If battery 1136 is permanent and not rechargeable, charging coil 1144 would be unnecessary.

Both of telemetry antennas 1142*a* and 1142*b* can be used to transcutaneously communicate data through the patient's tissue to an external device, but are different in shape and in the electromagnetic fields they employ. Telemetry antenna 1142*a* comprises a coil, which can bi-directionally communicate with an external device via a magnetic induction communication link, which comprises a magnetic field of typically less than 10 MHz operable in its near-field to communicate at a distance of 12 inches or less for example. Circuitry 1146 includes telemetry circuitry coupled to the coil antenna 1142*a*, including driver circuitry for energizing the coil antenna 1142*a* to transmit data and receiver circuitry for resolving data received at the coil 1142*a*. Such telemetry circuitry also operates in accordance with a modulation scheme (defining how data to be transmitted is modulated, and will be demodulated when received) and a communication protocol (defining the manner in which the data is formatted). A typical modulation scheme used for magnetic induction communications via coil antenna 1142*a* is Frequency Shift Keying (FSK), although other modulation schemes could also be used.

Telemetry antenna 1142*b* comprises a short-range Radio-Frequency (RF) antenna that operates in accordance with a short-range RF communication standard and its underlying modulation scheme and protocol to bi-directionally communicate with an external device along a short-range RF communication link. Short-range RF communication link typically operates using far-field electromagnetic waves ranging from 10 MHz to 10 GHz or so, and allows communications between devices at distances of about 50 feet or less. Short-range RF standards operable with antenna 42*b* include, for example, Bluetooth, BLE, NFC, Zigbee, WiFi (802.11x), and the Medical Implant Communication Service or the Medical Device Radiocommunications Service (both collectively referred to herein as "MICS" for short). Short-range RF antenna 1142*b* can take any number of well-known forms for an electromagnetic antenna, such as patches, slots, wires, etc., and can operate as a dipole or a monopole. Circuitry 1146 would include telemetry circuitry coupled to the short-range RF antenna 1142*b*, again including driver and receiver circuitry.

IPG 1101 could contain both the coil antenna 1142*a* and the short-range RF antenna 1142*b* to broaden the types of external devices with which the IPG 1101 can communicate, although IPG 1101 may also include only one of antenna 1142*a* and 1142*b*.

Examples of external devices operable to communicate with the IPG 1101 include external devices used to adjust the therapy settings the SMI 300 will provide to the patient. The therapy may require pulsing the light source to provide light pulses having a particular duration, pulse width, recovery time, etc. For example, the IPG 1101 may be programmed to cause the light source to be on for 5-10 seconds and off for a minute. That cycle may be repeated continually for a number of hours, days, or indefinitely. Upon evaluation, the physician may decide to reprogram the IPG 1101 to deliver a different pattern of therapy and may use an external device to communicate with the IPG 1101 to implement that change.

Figure 1:
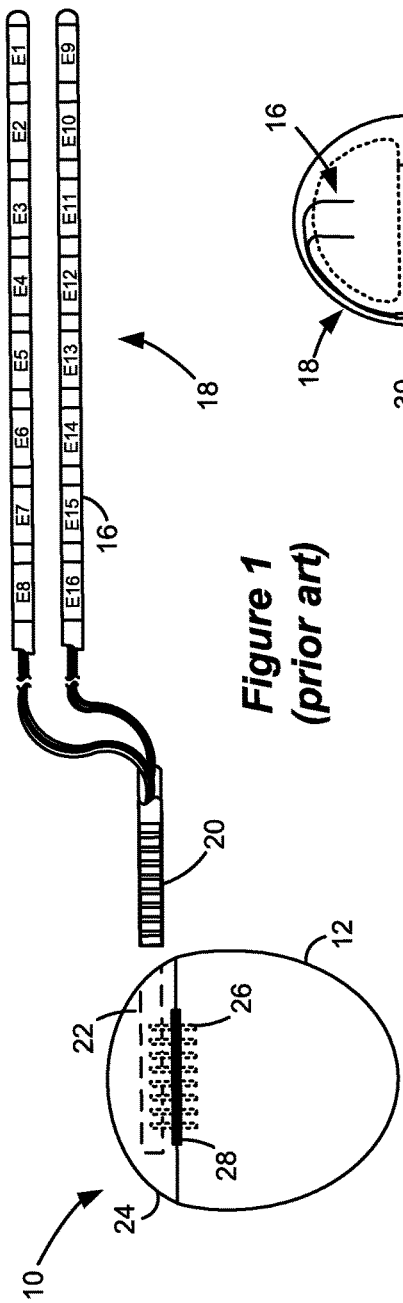
FIG. 1 shows an Implantable Pulse Generator such as a Deep Brain Stimulator (DBS), in accordance with the prior art.
Figure 2:
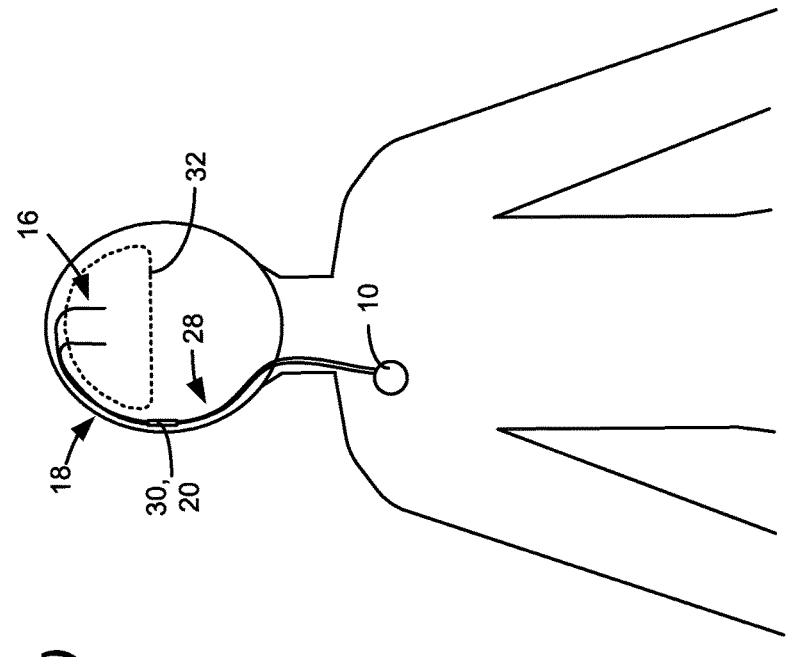
FIG. 2 shows the IPG of FIG. 1 as implanted in a patient, in accordance with the prior art.

According to some embodiments, phototherapy can be combined with electrical neuromodulation. For example, the patient may be fitted with one or more DBS electrode leads 18 (FIGS. 1 and 2) in addition to an SMI 300. In such an instance, the IPG 1101 is configured to control both the electro-active electrode leads and the SMI 300.

Figure 13:
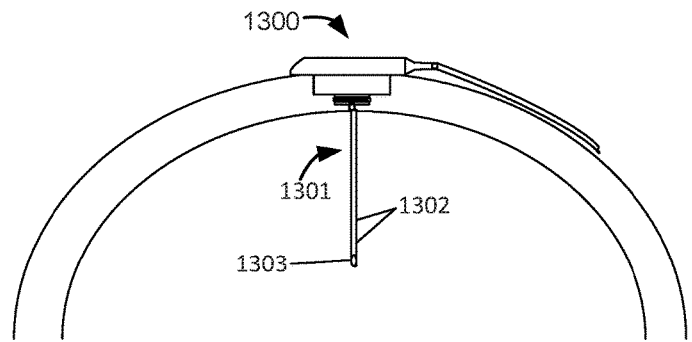
FIG. 13 shows an SMI configured to provide phototherapy and electrical neuromodulation.
Figure 14:
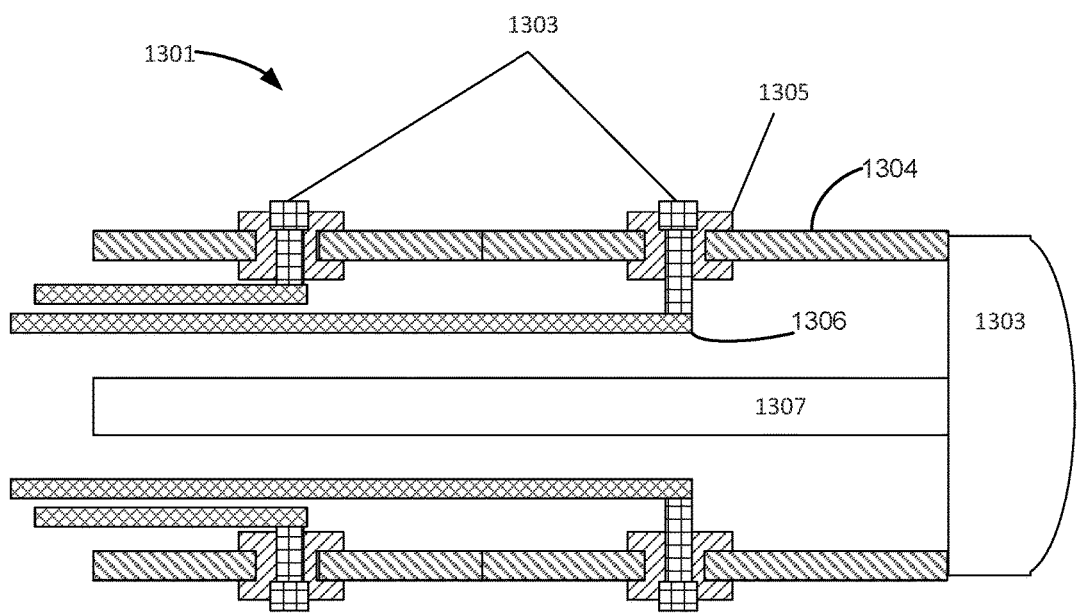
FIG. 14 shows a light pipe for an SMI that includes electrodes for providing electrical neuromodulation.

According to other embodiments, the SMI can be configured to provide both phototherapy and electrical neuromodulation. FIGS. 13 and 14 illustrate an SMI 1300 that includes a light pipe 1301 configured with electrodes 1302 and a diffuser 1303. The electrodes 1303 may be ring electrodes, for example, and may be insulated from the body 1304 of the light pipe 1301 by insulators 1305. The electrodes can be connected to the IPG 1101 by lead wires 1306. The light pipe 1301 illustrated in FIG. 14 includes a light guide 1307, such as an optical fiber. As described above, the light pipe may simply be a tube having a diffuser.

FIGS. 15 and 16 illustrate an alternative embodiment of an SMI 1500. Instead of being contained within an implant housing 1501, the light source 1502 is configured within an optical lead 1503, which replaces the light pipes illustrated in the earlier SMIs. The optical lead 1503 may attach to the implant housing 1501 similarly to the attachment of the light pipe to the implant housings described above, except that optical communication is not required. Instead, only electrical communication is required. A lead fitting 1504 containing electrical feedthroughs 1506 provides electrical communication between the implant housing 1501 and conductors 1505 attaching to the light source 1502. Configuring all or part of the light source within a an optical lead 1503 makes it possible to reduce the size of the SMI.

Power and signals from the IPG are communicated to the implant housing 1501 by a power lead 306. Within the implant housing 1501 the power and signals may be communicated to a PCB or other substrate 1507 via one or more feedthroughs 1508 and conductors 1509. According to some embodiments, the PCB or other substrate 1507 may include circuitry for driving/controlling the light source 1502. According to other embodiments, the PCB or other substrate may simply include conductors and/or feedthroughs for providing electrical contact with the conductors 1505.

FIG. 16 illustrates the light source 1502 in greater detail. The light source may include an LED 1601, such as an EPGAP 660 nm LED. The LED 1601 may be mounted to a two-pin feedthrough 1602 configured with pins 1603. The conductors 1505 connect to the pins 1603, which provide electrical power and signals to the LED 1601. The feedthrough 1602 may be a ceramic material, such as Kryoflex, for example. One or more connector plates may be used to mount the LED 1601 to the feedthrough 1602. In the illustrated embodiment, the mounting arrangement includes an insulating plate 1604 and a connecting plate 1605. The insulating plate 1604 may comprise a polymeric material, such as Kapton, for example.

The light source 1502 may further include a housing tube 1606 and an optical element 1607, such as a sapphire optical diffuser or lens. The housing tube 1606 may be titanium, for example. The optical element 1607 may be connected to the housing tube 1606 via a fitting 1608. The fitting 1608 may be a ceramic seal, such as Kryoflex, for example.

It should be appreciated that the embodiments having a light source contained within an optical lead can also be configured to include electrical stimulation, similarly to the embodiments illustrated in FIGS. 13 and 14. In such embodiments, the optical lead includes electrodes, such as ring electrodes and may contain additional conductors for communicating the electrical stimulation signals.

While the invention herein disclosed has been described by means of specific embodiments and applications thereof, numerous modifications and variations could be made thereto by those skilled in the art without departing from the scope of the invention set forth in the claims.

What is claimed is:

1. A medical device, comprising:
 a housing configured to mount to a patient's skull, wherein the housing comprises:
 a light source contained within the housing, and
 a light pipe fitting comprising a first window wherein the light pipe fitting is configured to accept a light pipe and a light pipe ferule,
 a light pipe ferule configured to hold a light pipe and comprising a second window and configured to hold a light pipe, and
 a light pipe, wherein
 the medical device is configured so that when the light pipe ferule and the light pipe are accepted within the light pipe fitting, the first and second windows provide a light path from the light source to the light pipe.

2. The medical device of claim 1, wherein the housing comprises a cylindrical portion configured to be recessed in a hole in a patient's skull.

3. The medical device of claim 1, wherein the housing comprises holes or partial holes configured to accept bone screws.

4. The medical device of claim 1, wherein the housing comprises an upper compartment and a hermetically sealed lower compartment.

5. The medical device of claim 4, further comprising one or more feedthroughs providing electrical communication between the upper compartment and the hermetically sealed lower compartment.

6. The medical device of claim 4, wherein the hermetically sealed lower compartment contains a printed circuit board (PCB) electrically connected to the light source.

7. The medical device of claim 6, further comprising a temperature sensor electrically connected to the PCB.

8. The medical device of claim 1, wherein the light pipe comprises a tubular member.

9. The medical device of claim 1, wherein the light pipe comprises a diffuser.

10. The medical device of claim 1, wherein the light pipe comprises a fiber optic member.

11. The medical device of claim 1, wherein the light pipe is interchangeable.

12. The medical device of claim 1, further comprising at least one electrode configured to provide electrical neuromodulation therapy.

13. The medical device of claim 12, wherein the at least one electrode is connected to the housing.

14. The medical device of claim 12, wherein the at least one electrode is integrated with the light pipe.

15. The medical device of claim 14, wherein the at least one electrode comprises one or more ring electrodes.

16. A system comprising a medical device and an implantable pulse generator (IPG), wherein:
 the medical device comprises:
 a housing configured to mount to a patient's skull, wherein the housing comprises:
 a light source contained within the housing, and
 a light pipe fitting comprising a first window and configured to accept a light pipe and a light pipe ferule,
 a light pipe ferule configured to hold a light pipe and comprising a second window and configured to hold a light pipe, and
 a light pipe, wherein
 the medical device is configured so that when the light pipe ferule and the light pipe are mounted within the light pipe fitting, the first and second windows provide a light path from the light source to the light pipe; and wherein
 the IPG comprises:
 a conductive IPG housing;
 electronic circuitry within the IPG housing; and
 at least one electrode wire cable extending outwardly from the IPG housing, wherein each electrode wire cable comprises a plurality of wires connected to the electronic circuitry, wherein the IPG is connected to the skull-mounted housing by the at least one electrode wire cable.

17. The medical device of claim 16, wherein the one or more of the plurality of wires are connected to a PCB within the skull-mounted housing via feedthroughs.

18. The medical device of claim 16, wherein the IPG comprises at least one battery.

19. The medical device of claim 16, wherein the at least one battery is rechargeable and the IPG comprises an internal charging coil antenna configured receive magnetic field to provide power for recharging the battery.

20. The medical device of claim 16, wherein the IPG comprises a data antenna configured to receive and/or transmit data to an external controller, wherein the data antenna is coupled to the electronic circuitry.

* * * * *